(12) United States Patent
Terakawa et al.

(10) Patent No.: US 8,400,710 B2
(45) Date of Patent: Mar. 19, 2013

(54) OBSERVING DEVICE

(75) Inventors: Susumu Terakawa, Hamamatsu (JP);
Takashi Sakurai, Hamamatsu (JP);
Hisao Osawa, Kashiwa (JP); Yasujiro Kiyota, Tokyo (JP)

(73) Assignee: Nikon Corporation, Tokyo (JP)

( * ) Notice: Subject to any disclaimer, the term of this patent is extended or adjusted under 35 U.S.C. 154(b) by 895 days.

(21) Appl. No.: 12/085,197

(22) PCT Filed: Nov. 29, 2006

(86) PCT No.: PCT/JP2006/323837
§ 371 (c)(1),
(2), (4) Date: May 19, 2008

(87) PCT Pub. No.: WO2007/063909
PCT Pub. Date: Jun. 7, 2007

(65) Prior Publication Data
US 2009/0273829 A1    Nov. 5, 2009

(30) Foreign Application Priority Data

Nov. 30, 2005 (JP) ................. 2005-345418

(51) Int. Cl.
*G02B 21/06* (2006.01)
(52) U.S. Cl. ........................ 359/389; 359/559
(58) Field of Classification Search ............ 359/385, 359/386, 559, 562, 565, 601, 614, 885, 896, 359/389
See application file for complete search history.

(56) References Cited

U.S. PATENT DOCUMENTS 2,105,671 A * 1/1938 Siegfried ............... 359/386
5,440,426 A * 8/1995 Sandstrom ............. 359/559
(Continued)

FOREIGN PATENT DOCUMENTS

| JP | A-11-337828 | 12/1999 |
| JP | A-2000-502472 | 2/2000 |

(Continued)

OTHER PUBLICATIONS

Komatsu, Hiroshi, "Fundamentals and Application of Optical Microscopy (3)," Applied Physics, Oct. 10, 1991, vol. 60, No. 10, pp. 1030-1034.

(Continued)

*Primary Examiner* — Frank Font
(74) *Attorney, Agent, or Firm* — Oliff & Berridge, PLC (57) ABSTRACT

The observing apparatus is being equipped with an image-forming optical system which forms an image of light emitted from a specimen, an imaging unit which picks up the image of the specimen formed by the image-forming optical system, and an illuminating unit which illuminates the specimen with a surface illuminant in which bright areas and dark areas are arranged alternately in order to provide an observing apparatus suitable to observe a transparent specimen with a wide field of view. If the position of the surface illuminant and the pitch of contrasting are set properly, each partial area of the specimen is illuminated obliquely at a small angle by each bright area of the surface illuminant. Therefore, the imaging unit can acquire a dark-field observation image of each partial area.

9 Claims, 7 Drawing Sheets

U.S. PATENT DOCUMENTS

| | | | |
|---|---|---|---|
| 5,548,441 A * | 8/1996 | Greenberg | 359/390 |
| 5,617,203 A | 4/1997 | Kobayashi et al. | |
| 5,673,144 A * | 9/1997 | Chastang et al. | 359/385 |
| 5,751,475 A * | 5/1998 | Ishiwata et al. | 359/387 |
| 6,239,909 B1 | 5/2001 | Hayashi et al. | |
| 6,243,197 B1 * | 6/2001 | Schalz | 359/388 |
| 7,345,754 B1 * | 3/2008 | Zhao et al. | 356/237.5 |
| 7,359,117 B2 * | 4/2008 | Shimizu et al. | 359/388 |
| 7,379,238 B2 * | 5/2008 | Ganser et al. | 359/381 |
| 7,471,435 B2 * | 12/2008 | Modavis | 359/227 |

FOREIGN PATENT DOCUMENTS

| | | |
|---|---|---|
| JP | A-2002-182008 | 6/2002 |
| JP | A-2002-311335 | 10/2002 |
| JP | A-2003-75725 | 3/2003 |
| JP | A-2003-84206 | 3/2003 |
| JP | A-2006-171025 | 6/2006 |
| WO | WO 2006/104184 A1 | 10/2006 |

OTHER PUBLICATIONS

Komatsu, Hiroshi, "Fundamentals and Application of Optical Microscopy (4)," Applied Physics, Nov. 10, 1991, vol. 60, No. 11, pp. 1136-1140.

Jul. 19, 2011 Office Action issued in JP Application No. 2006-321989 (with English translation).

Su et al., "Automated phase-measuring profilometry using defocused projection of a Ronchi grating," *Optics Communications*, Dec. 15, 1992, pp. 561-573, vol. 94, No. 6, Elsevier Science Publishers B.V., North-Holland.

Jan. 17, 2013 Search Report issued in European Application No. EP 06 83 3640.

* cited by examiner

OBSERVING DEVICE

CROSS-REFERENCE TO RELATED APPLICATION

This application is a U.S. National Stage application claiming the benefit of prior filed International Application Number PCT/JP2006/323837, filed Nov. 29, 2006, in which the International Application claims a priority date of Nov. 30, 2005, based on prior filed Japanese Application Number 2005-345418, the entire contents of which are incorporated herein by reference.

TECHNICAL FIELD

The present invention relates to an observing apparatus for observing a transparent specimen.

BACKGROUND ART

To observe a transparent specimen such as cells in a culture container, the phase contrast observation (refer to Non-patent Documents 1 and 2, for example) which can visualize its refractive index distribution is used suitably. To observe a transparent specimen which cannot be observed with naked eyes, a microscope or some other optical system is necessary even if the observation is intended to check the entire specimen roughly.

NON-patent Document 1: Hiroshi Komatsu, "Fundamentals and Application of Optical Microscopy (3)," Applied Physics, Vol. 60, No. 10, pp. 1,032-1,034, 1991

NON-patent Document 2: Hiroshi Komatsu, " Fundamentals and Application of Optical Microscopy (4)," Applied Physics, Vol. 60, No. 11, pp. 1,136-1,138, 1991

DISCLOSURE

Problems to be Solved

However, there are no phase contrast microscopes having such a wide field of view as to enable observation of the entire area of a culture container at one time. If one attempted to realize such a phase contrast microscope, it would be extremely costly because a very large image-forming optical system for phase contrast observation and a very large zonal illuminating optical system are necessary.

To observe the entire specimen only roughly, one option is to perform dark-field observation instead of phase contrast observation. In the dark-field observation, faint diffraction light (scattered light) generated by refractive index bounds in a specimen is detected and an observation image is formed by using only the diffraction light.

However, if the field of view of a dark-field microscope is widened, the illumination angle is increased and an observation image can only be formed from very faint diffraction light that is emitted from a specimen at large angles. Therefore, the brightness of the observation image is far too low. Furthermore, where the illumination angle is large, there may occur a case that strong light generated by the edge, bottom, or the like of a culture container enters the image-forming optical system and obstructs the observation.

An object of the present invention is therefore to provide an observing apparatus suitable to observe a transparent specimen with a wide field of view.

Means for Solving the Problems

An observing apparatus according to the invention including an illuminating unit which illuminates a specimen with a surface illuminant in which bright areas and dark areas are arranged alternately; an image-forming optical system which forms an image of light that passes through the specimen being illuminated by the illuminating unit; and an imaging unit which picks up the image formed by the image-forming optical system.

It is desirable that the distance d between the surface illuminant and the specimen and the pitch P of contrasting of the surface illuminant satisfy an inequality $$\frac{P}{d} \leq \sqrt{2(1 - 0.02/NA^2)}$$

where NA is an object-side numerical aperture of the image-forming optical system.

It is desirable that the distance d between the surface illuminant and the specimen and the pitch P of contrasting of the surface illuminant satisfy an inequality $$\frac{P}{d} \leq 2 \cdot NA'$$

where NA' is an image-side numerical aperture of the image-forming optical system.

Furthermore, it is desirable that the distance d between the surface illuminant and the specimen and the pitch P of contrasting of the surface illuminant satisfy an inequality $$\frac{\lambda}{2 \cdot a \cdot NA} \leq \frac{P}{d}$$

where NA is an object-side numerical aperture of the image-forming optical system, $\lambda$ is a wavelength of the surface illuminant, and a is a distance between an image-side principal plane of the image-forming optical system and the imaging unit.

The illuminating unit may include a surface illuminant which emits light with an approximately uniform intensity distribution and a mask which is disposed on the surface illuminant and in which aperture areas and masking areas are arranged alternately.

The illuminating unit may include a liquid crystal spatial light modulator.

The observing apparatus according to the invention may further include an image processing unit which removes a component of an image of the surface illuminant from the image of the specimen acquired by the imaging unit.

The observing apparatus according to the invention may further include a unit which varies the phase of contrasting of the surface illuminant.

The observing apparatus according to the invention may further include a unit which varies the pitch of contrasting of the surface illuminant.

Furthermore, the observing apparatus according to the invention may further include a unit which varies the duty ratio of contrasting of the surface illuminant.

The invention realizes an observing apparatus suitable to observe a transparent specimen with a wide field of view.

DETAILED DESCRIPTION OF THE EMBODIMENTS

[First Embodiment]

A first embodiment will be described below. This embodiment is an embodiment of an observing apparatus.

Figure 1:
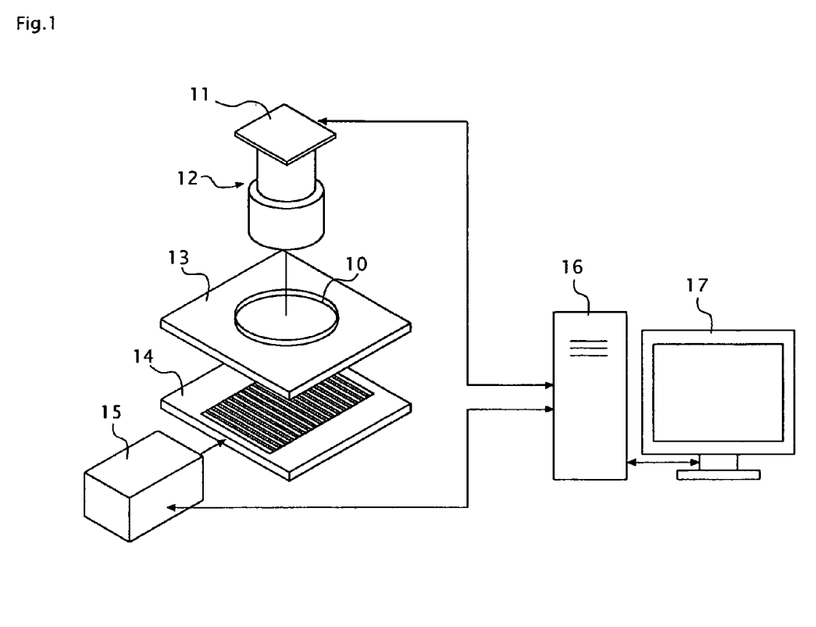
FIG. 1 shows the entire configuration of an observing apparatus.

FIG. 1 shows the entire configuration of this observing apparatus. As shown in FIG. 1, this observing apparatus is equipped with a transmission-type liquid crystal panel 14 having a backlight, a stage (table for a specimen) 13, an image-forming optical system 12, an imaging sensor 11, a controller 15 for the transmission-type liquid crystal panel, a computer 16, a display 17, etc.

A transparent observation object 10 is placed on the stage 13. For example, the observation object 10 is a transparent culture container (e.g., a petri dish of 35 mm in diameter) containing unstained cells.

The transmission-type liquid crystal panel 14 illuminates approximately the entire area of the observation object 10. So as not to interrupt illumination light, the portion of the stage 13 on which the observation object 10 is placed is made of a transparent material such as glass or is made hollow.

The image-forming optical system 12 has a sufficiently wide field of view, and light emitted from approximately the entire area of the observation object 10 is collected by the image-forming optical system 12 and image-formed on the imaging plane of the imaging sensor 11. The image sensor 11 picks up an image (brightness distribution) on the imaging plane according to an instruction from the computer 16. The image is taken in by the computer 16 and displayed on the display 17 after being subjected to image processing.

When necessary, the computer 16 can store an image that has or has not been subjected to image processing. When necessary, an image that has not been subjected to image processing can be displayed on the display 17.

According to an instruction from the computer 16, the controller 15 displays, on the transmission-type liquid crystal panel 14, a pattern in which bright areas and dark areas are arranged alternately. In this embodiment, this pattern is a striped pattern. At this time, a striped surface illuminant is formed on the transmission-type liquid crystal panel 14.

The pitch P of contrasting of this surface illuminant is sufficiently longer than the size (10 to 15 μm) of a phase object (cells) as a subject of observation, and the distance d between the surface illuminant and the observation object 10 is properly so long that the surface illuminant is out of the depth of filed of the image-forming optical system 12. The relationship between the pitch P and the distance d is set so as to satisfy the following three conditions:

(Condition 1) The angle that is subtended at a partial area on the observation object 10 opposed squarely to a dark area of the surface illuminant by two bright areas on both sides of the dark area is sufficiently small.

(Condition 2) Both of bright areas and dark areas of the surface illuminant surely exist in the field of view of the image-forming optical system 12.

(Condition 3) The presence of bright areas and dark areas of the surface illuminant can be recognized reliably on the imaging sensor 11.

The details of the conditions 1-3 will be described later.

In particular, in this embodiment, it is assumed that bright areas and dark areas of the surface illuminant exist in tens of pitches in the field of view of the image-forming optical system 12 and that the bright area width/dark area width ratio (duty ratio) of the surface illuminant is 50%. It is also assumed that a surface illuminant image on the imaging sensor 11 is blurred to a proper extent and that the brightness distribution curve of the surface illuminant image in the pitch direction assumes a sinusoidal wave. That is, the illuminance of a surface illuminant image on an observation plane 10a is approximately uniform. The display pattern on the transmission-type liquid crystal panel 14 may be either a binary pattern or a grayscale pattern.

Figure 2:
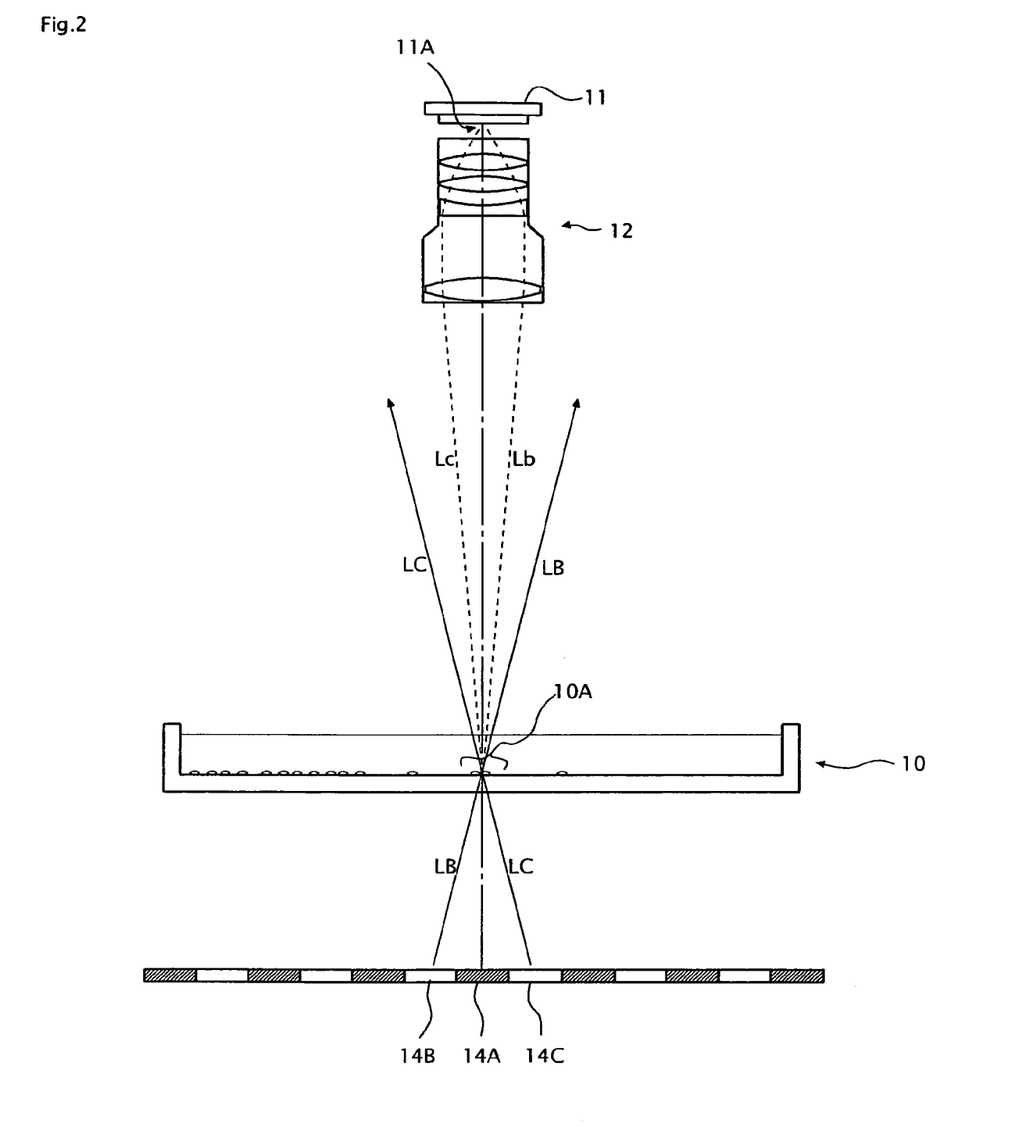
FIG. 2 is a conceptual diagram illustrating the operation of an optical system part of the observing apparatus.

FIG. 2 is a conceptual diagram illustrating the operation of an optical system part of this observing apparatus. FIG. 2 conceptually shows the optical system part of this observing apparatus.

First, a description will be made with attention paid to a certain dark area 14A on the surface illuminant and a partial area 10A on the observation object 10 that is squarely opposed to the dark area 14A.

Light beams LB and LC that are emitted from two respective bright areas 14B and 14C that are adjacent to the dark area 14A shine on the partial area 10A. No light beam coming from the dark area 14A shines on the partial area 10A. Therefore, the partial area 10A is illuminated obliquely by the light beams LB and LC.

Whereas parts of the incident light beams LB and LC pass through the partial area 10A as they are, that is, without being diffracted, the other parts of the light beams LB and LC are diffracted (or scattered) being influenced by refractive index bounds in the partial area 10A. Undiffracted light beams LB and LC that have merely passed through the partial area 10A do not enter the pupil of the image-forming optical system 12. On the other hand, diffracted (or scattered) light beams Lb and Lc generated by the partial area 10A enter the pupil of the image-forming optical system 12.

At this time, an image of the dark area 14A and an image (hereinafter referred to as "observation image") of the outline of a phase object existing in the partial area 10A are formed in superimposition in an area 11A on the imaging sensor 11 that is conjugate with the partial area 10A. That is, a dark-field image of the partial area 10A is formed.

The angle that is subtended at the partial area 10A by the two bright areas 14B and 14C is sufficiently small. Therefore, the angles at which the area 10A is illuminated with the light beams LB and LC are also sufficiently small. At this time, the observation image of the partial area 10A is generated by the high-intensity diffraction lights Lb and Lc that are emitted at small angles. Therefore, the observation image of the partial area 10A is sufficiently bright.

Figure 3A:
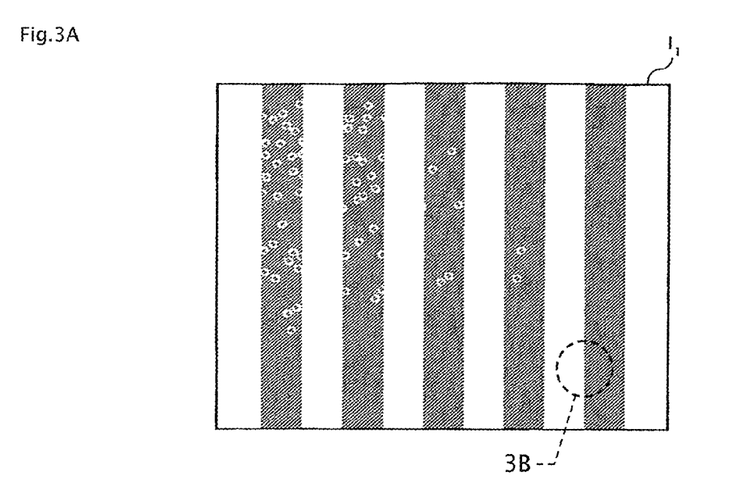
FIG. 3A shows an image $I_1$.
Figure 3B:
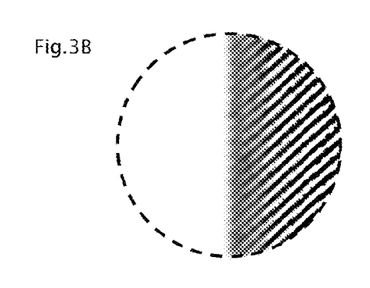
FIG. 3B shows a blurred boundary between a bright portion and a dark portion of the image $I_1$.

What has been described above also applies to each area of the observation object 10 that is squarely opposed to a corresponding dark area. Therefore, as shown in FIG. 3A, an image $I_1$ acquired by the imaging sensor 11 is such that an observation image is superimposed on a striped dark background. Although in FIG. 3A the boundaries between the bright portions and the dark portions of the surface illuminant image are drawn as sharp lines, FIG. 3B provides a magnified view illustrating that the boundaries are blurred actually.

A user can easily observe the observation object 10 by displaying the image $I_1$ on the display 17 by the computer 16.

However, the image $I_1$ includes only the observation image of the areas that account for about a half of the total area of the observation object 10 (i.e., only the observation image of the areas that are squarely opposed to the dark areas). Furthermore, the contrast of the observation image is low because the background of the observation image is not a complete dark background and has a sinusoidal brightness distribution.

Therefore, the computer 16 of this observing apparatus executes the following process to allow an approximately entire area of the observation object 10 to be observed with high contrast.

(Step 1) Displays a striped surface illuminant (duty ratio: 50%) on the transmission-type liquid crystal panel 14 and acquires an image $I_1$ as shown in FIG. 3A in this state.

Figure 4:
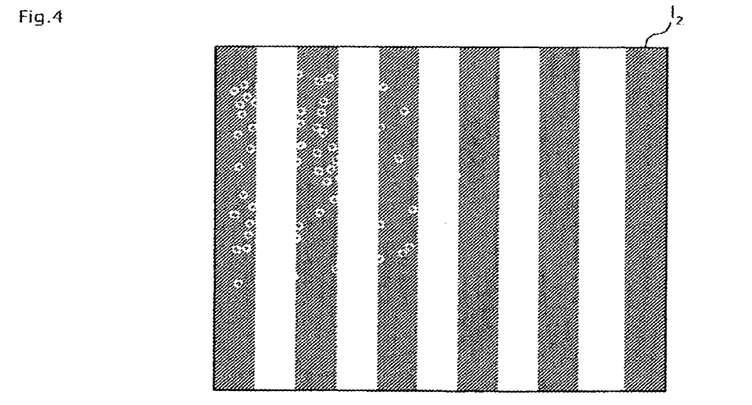
FIG. 4 shows an image $I_2$.
Figure 5:
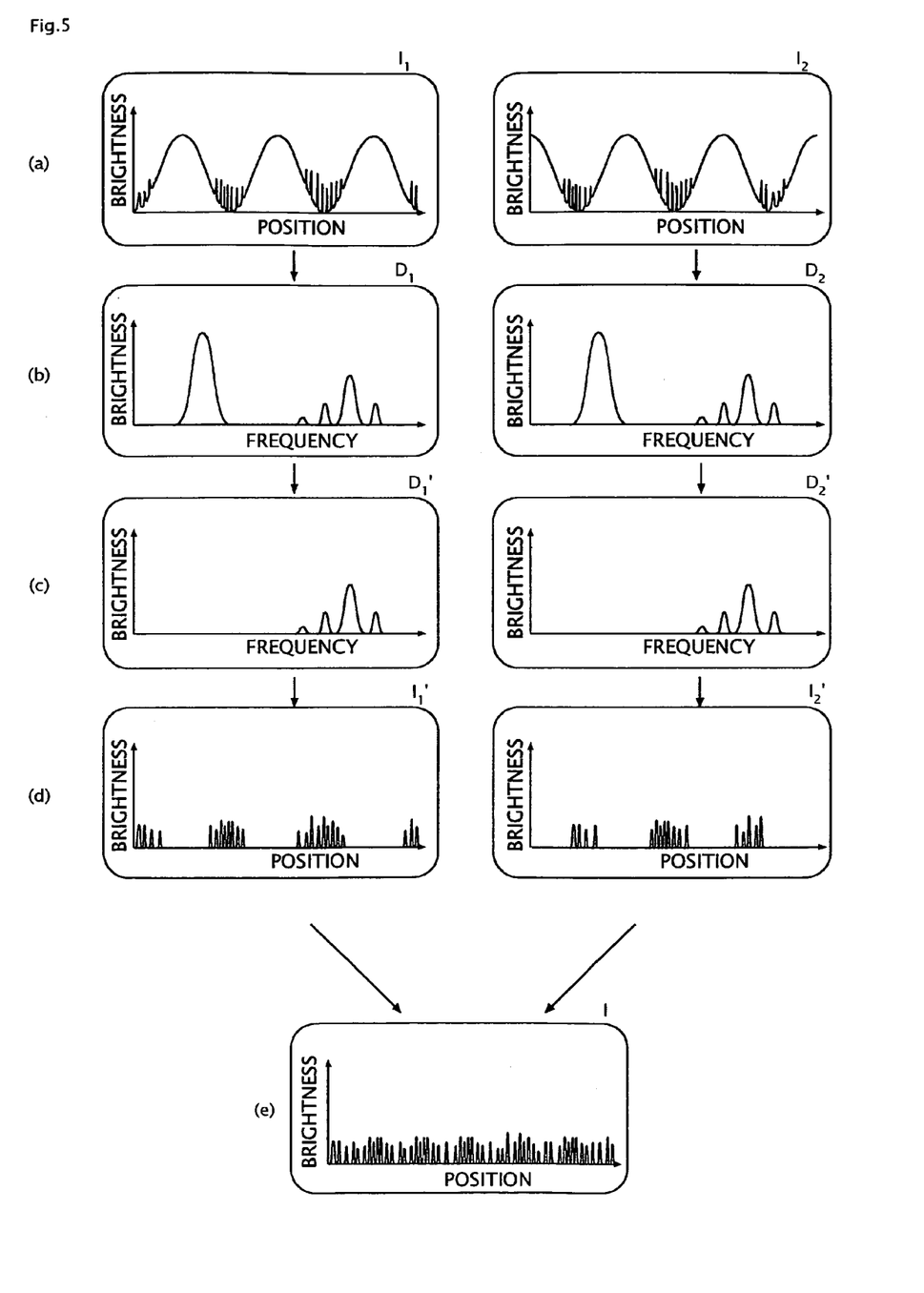
FIG. 5 illustrates the procedure of image processing which is performed by a computer 16 in a first embodiment.

(Step 2) Shifts the phase of contrasting of the surface illuminant by $\pi$ and acquires an image $I_2$ as shown in FIG. 4 in this state. The image $I_2$ includes an observation image of different areas from the image $I_1$ does. FIG. 5(a) conceptually shows brightness distributions of the images $I_1$ and $I_2$ in the direction of the pitch of contrasting.

(Step 3) As shown in FIGS. 5(a) and 5(b), performs spatial Fourier transform on the images $I_1$ and $I_2$ individually and thereby obtains data $D_1$ representing spatial frequency components of the image $I_1$ and data $D_2$ representing spatial frequency components of the image $I_2$. In each of the data $D_1$ and $D_2$, the large peak on the low frequency side is a component of the surface illuminant image and plural small peaks on the high frequency side are components of the observation image.

(Step 4) As shown in FIGS. 5(b) and 5(c), removes the component of the surface illuminant image from each of the data $D_1$ and $D_2$ and thereby obtains data $D_1'$ and $D_2'$.

(Step 5) As shown in FIGS. 5(c) and 5(d), performs inverse Fourier transform on the data $D_1'$ and $D_2'$ individually and thereby obtains images $I_1'$ and $I_2'$. Each of the images $I_1'$ and $I_2'$ includes only the observation image, that is, it does not include the surface illuminant image.

(Step 6) As shown in FIGS. 5(d) and 5(e), combines the images and $I_1'$ and $I_2'$ together and thereby obtains a single image I. The image I is displayed on the display 17.

The image I includes an observation image of an approximately entire area of the observation object 10 and its background is black. Therefore, a user can observe the approximately entire area of the observation object 10 with high contrast as a dark-field image.

[Second Embodiment]

A second embodiment will be described below. Only differences from the first embodiment will be described. The differences reside in the procedure of the process that is executed by the computer 16. The process according to this embodiment is as follows.

Figure 6:
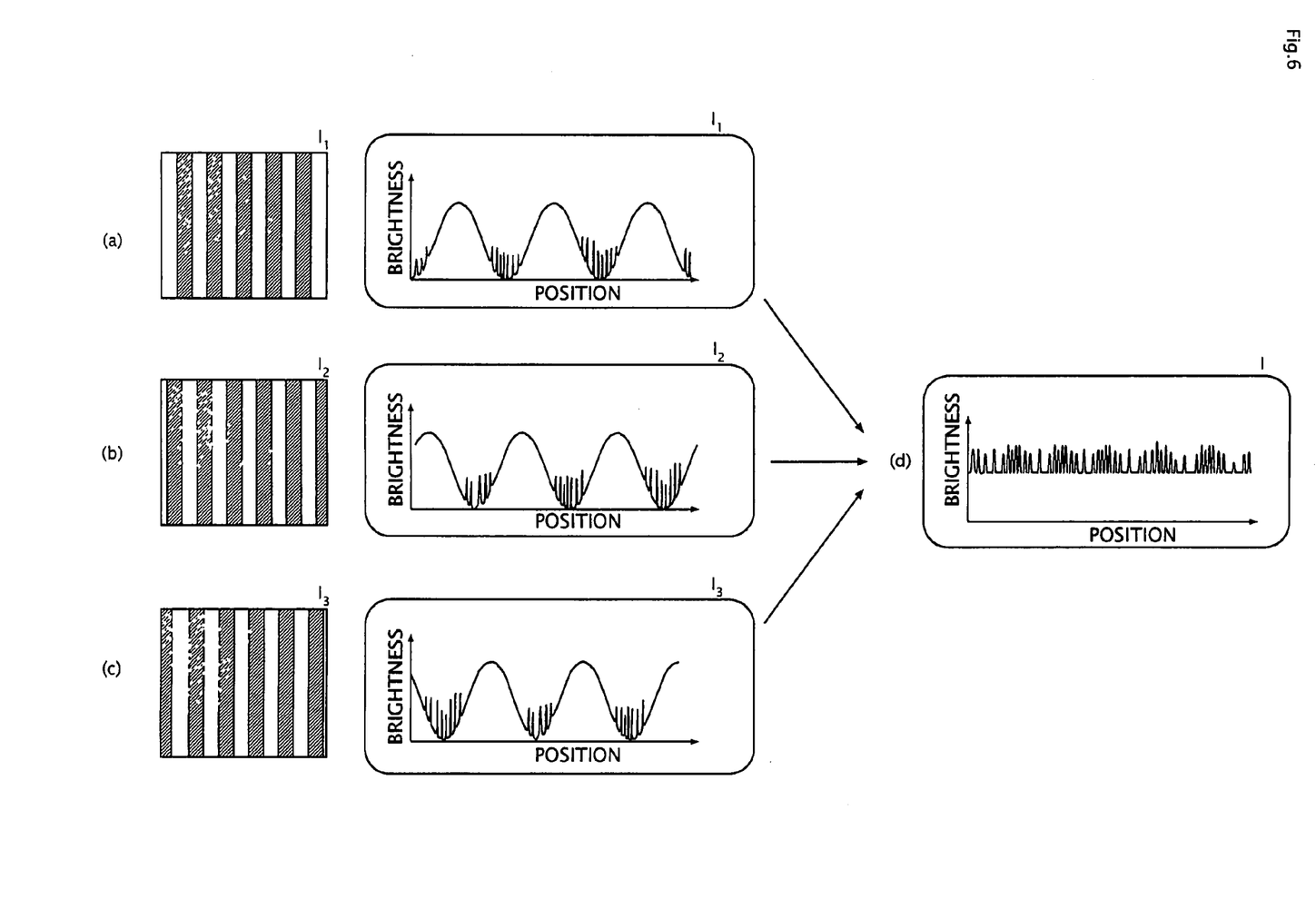
FIG. 6 illustrates the procedure of image processing which is performed by the computer 16 in a second embodiment.

(Step 1) Displays a striped surface illuminant (duty ratio: 50%) on the transmission-type liquid crystal panel 14 and acquires an image $I_1$ as shown in FIG. 6(a) in this state.

(Step 2) Shifts the phase of contrasting of the surface illuminant by $2\pi/3$ and acquires an image $I_2$ as shown in FIG. 6(b) in this state.

(Step 3) Shifts the phase of contrasting of the surface illuminant further by $2\pi/3$ and acquires an image $I_3$ as shown in FIG. 6(c) in this state.

(Step 4) Obtains a single image I as shown in FIG. 6(d) by substituting the images $I_1$, $I_2$, and $I_3$ into the following calculation formula (1) on a pixel-by-pixel basis.

$$I=\sqrt{(I_1-I_2)^2+(I_2-I_3)^2+(I_3-I_1)^2} \quad (1)$$

The image I includes an observation image of an approximately entire area of the observation object 10 and its background is uniform in brightness. To make the background black, the computer 16 removes, from the image I, the component (0th component) whose spatial frequency is zero. The computer 16 displays a resulting image on the display 17.

The resulting image, the 0th-component-removed image, includes an observation image of an approximately entire area of the observation object 10 and its background is black. Therefore, a user can observe the approximately entire area of the observation object 10 with high contrast as a dark-field image.

In this embodiment, a simpler calculation formula (1') may be used in place of the calculation formula (1):

$$I=I_1+I_2+I_3 \quad (1')$$

[Conditions 1, 2, and 3]

The details of the conditions 1, 2, and 3 will be described below.

Figure 7:
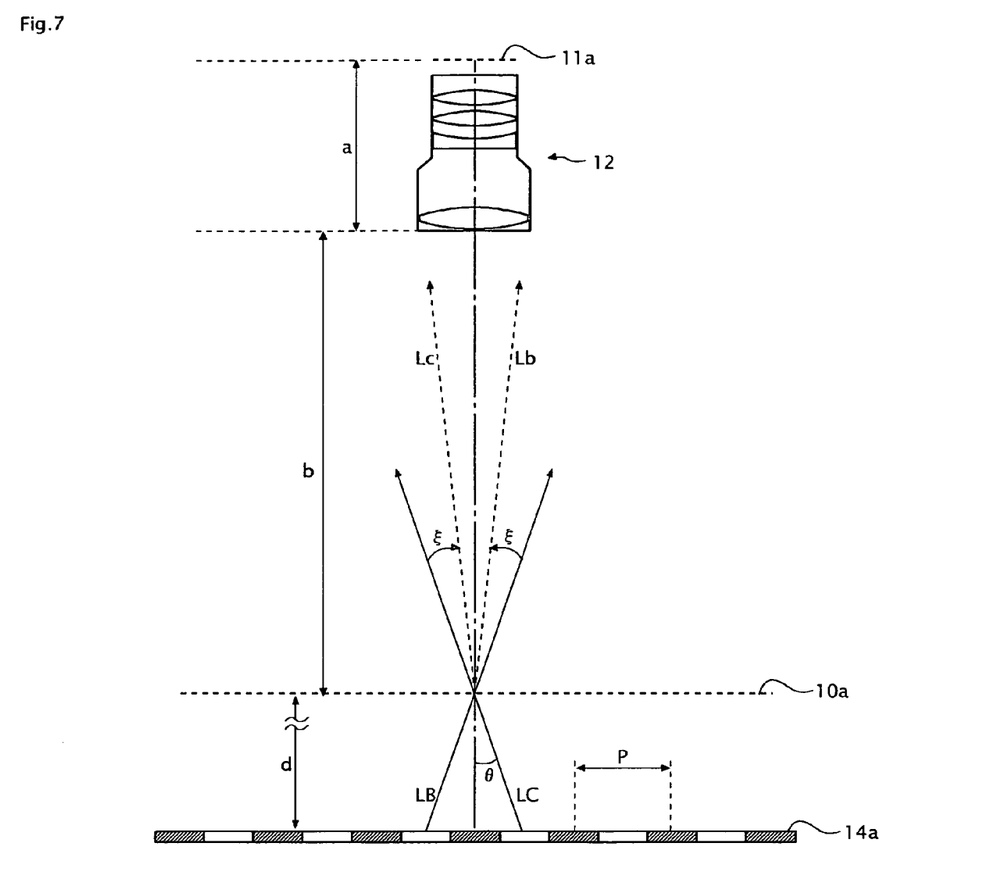
FIG. 7 illustrates conditions 1, 2, and 3.

FIG. 7 illustrates the conditions 1, 2, and 3. In FIG. 7, reference symbol 11a denotes an imaging plane of the imaging sensor 11, symbol 10a denotes a focal plane (i.e., observation plane) of the image-forming optical system 12, and symbol 14a denotes a plane on which a surface illuminant is formed (i.e., light source plane).

(Condition 1)

First, the angle that is subtended at a point on the observation plane 10a by a dark area 14A and a bright area 14C is represented by $\theta$. The angle $\theta$ corresponds to the incident angle of two light beams LC and LB which shine on the observation plane 10a.

The diffraction angle of diffraction lights Lc and Lb that originate from the observation plane 10a and can enter the pupil of the image-forming optical system 12 is an angle $\xi$ that satisfies all of the following formulae (2), (3), and (4) at the same time:

$$\cos\xi = \cos\theta\cdot\cos\rho + \sin\theta\cdot\sin\rho\cdot\cos\phi \quad (2)$$

$$0 \leq \rho \leq NA \quad (3)$$

$$0 \leq \phi \leq 2\pi \quad (4)$$

Characters NA represent the object-side numerical aperture of the image-forming optical system 12, and approximation is possible by regarding it as sufficiently small.

From Formulae (2)-(4), the ratio R of the light quantity of the diffraction lights Lc and Lb to that of the light beams LC and LB which shine on the observation plane 10a is given by Equation (5):

$$R = \frac{1}{2} \cdot \int \cos\xi \cdot d\rho \cdot d\varphi \quad (5)$$

$$= \frac{1}{2} \cdot NA^2 \cdot \cos\theta$$

An observation image is given sufficient brightness if the light quantity ratio R is sufficiently large. To this end, the light quantity ratio R needs to satisfy at least the following Inequality (6):

$$R \geq 0.01 \quad (6)$$

Inequality (7) is obtained by substituting Equation (5) into Inequality (6):

$$\frac{1}{2} \cdot NA^2 \cdot \cos\theta \geq 0.01 \quad (7)$$

The angle θ is given by the following Equation (8) which includes the distance d from the light source plane 14a to the observation plane 10a and the pitch P of contrasting of the surface illuminant. Approximation is made by regarding θ as sufficiently small.

$$\theta = \left(\frac{P}{2}\right)/d \quad (8)$$

Inequality (9) is obtained by substituting Equation (8) into Inequality (7). Approximation is made by regarding θ as sufficiently small (an approximation formula $\cos\theta \approx 1 - \theta^2/2$ is used).

$$\frac{P}{d} \leq \sqrt{2(1 - 0.02/NA^2)} \quad (9)$$

Inequality (9) is a condition formula corresponding to the condition 1.

(Condition 2)

First, the width Z of a region in the light source plane 14a that fits in the field of view of the image-forming optical system 12 is given by Equation (10):

$$Z = 2 \cdot NA' \times d \quad (10)$$

where NA' is the image-side numerical aperture of the image-forming optical system 12.

For bright areas and dark areas of one or more pitches to exist in the region having the width Z in the light source plane 14a, Inequality (11) needs to be satisfied:

$$P \leq Z \quad (11)$$

Inequality (12) is obtained by substituting Equation (10) into Inequality (11):

$$\frac{P}{d} \leq 2 \cdot NA' \quad (12)$$

Inequality (12) is a condition formula corresponding to the condition 2.

(Condition 3)

First, for bright areas and dark areas in the light source plane 14a to be resolved from each other in the imaging plane 11a, the magnification M of the image-forming optical system 12 and the light source wavelength λ need to satisfy Inequality (13):

$$P \cdot M \geq \frac{\lambda}{2 \cdot NA} \quad (13)$$

The magnification M of the image-forming optical system 12 is given by the following Equation (14):

$$M = \frac{a}{b+d} \quad (14)$$

where a is the distance from the image-side principal plane of the image-forming optical system 12 to the imaging plane 11a and b is the distance from the image-side principal plane of the image-forming optical system 12 to the observation plane 10a.

Since d>>b, Equation (14) can be rewritten into Equation (15):

$$M = \frac{a}{d} \quad (15)$$

Inequality (16) is obtained by substituting Equation (15) into Inequality (13):

$$\frac{\lambda}{2 \cdot a \cdot NA} \leq \frac{P}{d} \quad (16)$$

Inequality (16) is a condition formula corresponding to the condition 3.

[Modifications to Each Embodiment]

Although each embodiment employs the controller and the transmission-type liquid crystal panel having a backlight to generate a surface illuminant, other devices may be used as long as they can generate a similar surface illuminant.

For example, many small light sources such as LEDs are prepared and arranged densely in array form, whereby a surface illuminant which emits light with an approximately uniform intensity distribution is formed. A masking member having striped apertures is disposed on the surface illuminant. As a result, a striped surface illuminant is formed. Incidentally, the phase of contrasting of the surface illuminant can be shifted by shifting the masking member in the direction of the pitch of contrasting. Instead of shifting the masking member, plural masking members having different aperture patterns may be prepared and switched.

Although in each embodiment the pitch of contrasting of the surface illuminant is fixed, the pitch may be varied according to the size of a phase object (cells) as a subject of observation. This makes it possible to properly observe phase objects (cells) having various sizes.

Although in each embodiment the duty ratio of contrasting of the surface illuminant is fixed, the duty ratio may be varied according to the refractive index of a phase object (cells) as a subject of observation. For example, when the refractive index of a phase object (cells) is large in which case the intensity of diffraction light is high, the proportion of dark areas may be increased (e.g., to 70% or 80%) to decrease the number of times of image acquisition accordingly. This is because an observation image in the same image occupies a larger area when the proportion of dark areas is high. On the other hand, when the refractive index of a phase object (cells) is small, it is possible to decrease the proportion of dark areas (e.g., to 30%) and increase the number of times of image acquisition accordingly.

Figure 8:
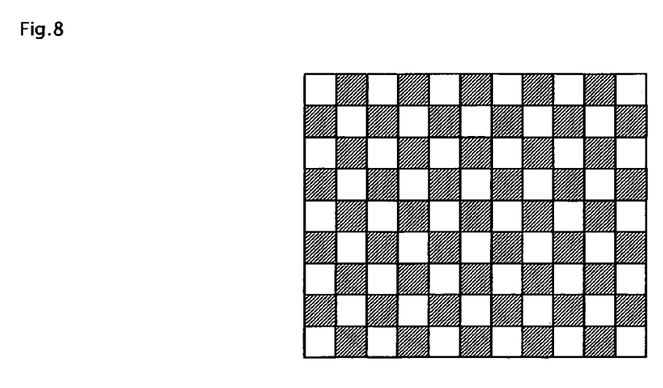
FIG. 8 shows a bright/dark pattern of a surface illuminant according to a modification.

Although in each embodiment the bright/dark pattern of the surface illuminant is a striped pattern, other patterns may be employed in which bright areas and dark areas are arranged alternately. For example, a checkered pattern as shown in FIG. 8 may be employed.

Figure 9:
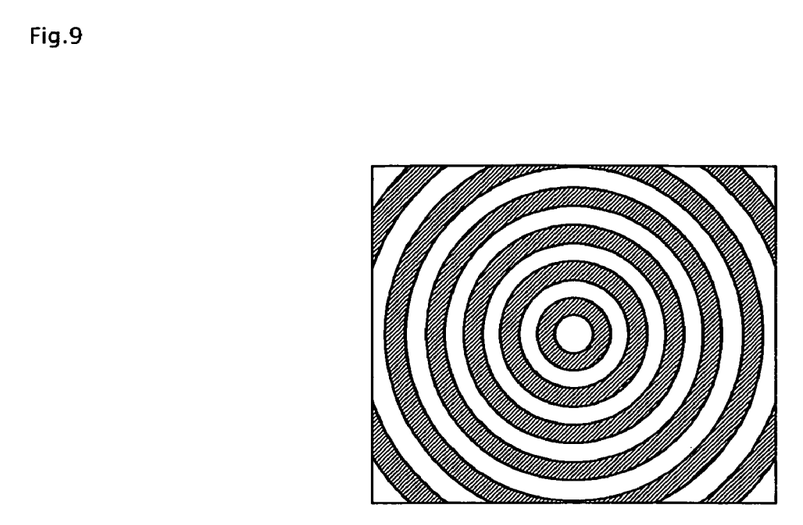
FIG. 9 shows a bright/dark pattern of a surface illuminant according to another modification.

A concentric pattern as shown in FIG. 9 may also be employed. In either case, the phase of contrasting can be shifted by varying the pattern in such a direction that the bright areas and the dark areas are reversed (in the radial direction in the case of the concentric pattern).

The employment of the striped pattern (FIG. 1) or the checkered pattern (FIG. 8) is preferable because it simplifies the phase shift processing and the image processing.

EXAMPLE 1

$NA \geq 0.14286$ $P = 6$ mm $d = 30$ mm

These numerical values satisfy the condition 1 (Inequality (9)).

EXAMPLE 2

$NA' \geq 0.1$ $P = 6$ mm $d = 30$ mm

These numerical values satisfy the condition 2 (Inequality (12)).

EXAMPLE 3

$NA \geq 0.003$ $P = 6$ mm $d = 30$ mm $a = 5$ mm $\lambda = 550$ nm $= 550 \times 10^{-4}$ mm These numerical values satisfy the condition 3 (Inequality (16)).

EXAMPLE 4

$NA \geq 0.14286$ $P = 6$ mm $d = 30$ mm $NA' \geq 0.1$ $a = 5$ mm $\lambda = 550$ nm $= 550 \times 10^{-4}$ mm These numerical values satisfy all of the condition 1 (Inequality (9)), the condition 2 (Inequality (12)), and the condition 3 (Inequality (16)).

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to exact construction and operation illustrated and described, and accordingly all suitable modifications and equivalents may be resorted to, falling within the scope thereof.

The invention claimed is:

1. An observing apparatus comprising:
an illuminating unit that illuminates a specimen with a surface illuminant in which bright areas and dark areas are arranged alternately;
an image-forming optical system that forms an image of light that passes through the specimen being illuminated by the illuminating unit;
an imaging unit that picks up the image formed by the image-forming optical system; and
an image of the surface illuminant that is formed on an imaging plane of the imaging unit by the image-forming optical system is blurred to an extent that a presence of the bright areas and the dark areas is recognizable, wherein
a distance d between the surface illuminant and the specimen and a pitch P of contrasting of the surface illuminant satisfy an inequality $$\frac{P}{d} \leq \sqrt{2(1 - 0.02/NA^2)}$$

where NA is an object-side numerical aperture of the image-forming optical system.

2. An observing apparatus comprising:
an illuminating unit that illuminates a specimen with a surface illuminant in which bright areas and dark areas are arranged alternately;
an image-forming optical system that forms an image of light that passes through the specimen being illuminated by the illuminating unit;
an imaging unit that picks up the image formed by the image-forming optical system; and
an image of the surface illuminant that is formed on an imaging plane of the imaging unit by the image-forming optical system is blurred to an extent that a presence of the bright areas and the dark areas is recognizable, wherein
a distance d between the surface illuminant and the specimen and a pitch P of contrasting of the surface illuminant satisfy an inequality $$\frac{P}{d} \leq 2 \cdot NA'$$

where NA' is an image-side numerical aperture of the image-forming optical system.

3. An observing apparatus comprising:
an illuminating unit that illuminates a specimen with a surface illuminant in which bright areas and dark areas are arranged alternately;
an image-forming optical system that forms an image of light that passes through the specimen being illuminated by the illuminating unit;
an imaging unit that picks up the image formed by the image-forming optical system; and
an image of the surface illuminant that is formed on an imaging plane of the imaging unit by the image-forming optical system is blurred to an extent that a presence of the bright areas and the dark areas is recognizable, wherein
a distance d between the surface illuminant and the specimen and a pitch P of contrasting of the surface illuminant satisfy an inequality $$\frac{\lambda}{2 \cdot a \cdot NA} \leq \frac{P}{d}$$

where NA is an object-side numerical aperture of the image-forming optical system, $\lambda$ is a wavelength of the surface illuminant, and a is a distance between an image-side principal plane of the image-forming optical system and the imaging unit.

4. The observing apparatus according to claim 1, wherein the illuminating unit comprises:
  a light source which emits light with an approximately uniform intensity distribution; and
  a mask which is disposed on the light source and in which aperture areas and masking areas are arranged alternately.

5. The observing apparatus according to claim 1, wherein the illuminating unit comprises a liquid crystal spatial light modulator.

6. The observing apparatus according to claim 1, further comprising an image processing unit which removes a component of an image of the surface illuminant from the image of the specimen acquired by the imaging unit.

7. The observing apparatus according to claim 1, further comprising a unit which varies a phase of contrasting of the surface illuminant.

8. The observing apparatus according to claim 1, further comprising a unit which varies a pitch of contrasting of the surface illuminant.

9. The observing apparatus according to claim 1, further comprising a unit which varies a duty ratio of contrasting of the surface illuminant.

\* \* \* \* \*